(12) United States Patent
Abbitt

(10) Patent No.: US 7,897,841 B2
(45) Date of Patent: Mar. 1, 2011

(54) SEED-PREFERRED REGULATORY ELEMENTS

(75) Inventor: Shane E. Abbitt, Ankeny, IA (US)

(73) Assignee: Pioneer Hi-Bred International, Inc., Johnston, IA (US)

(*) Notice: Subject to any disclaimer, the term of this patent is extended or adjusted under 35 U.S.C. 154(b) by 0 days.

(21) Appl. No.: 12/579,017

(22) Filed: Oct. 14, 2009

(65) Prior Publication Data

US 2010/0037347 A1 Feb. 11, 2010

Related U.S. Application Data

(63) Continuation of application No. 12/145,564, filed on Jun. 25, 2008, now Pat. No. 7,622,637.

(60) Provisional application No. 60/955,412, filed on Aug. 13, 2007.

(51) Int. Cl.
*A01H 5/00* (2006.01)
*C12N 15/82* (2006.01)
*C12N 15/87* (2006.01)
*C12N 15/63* (2006.01)

(52) U.S. Cl. ......... 800/295; 800/278; 800/287; 800/320; 800/320.1; 435/419; 435/468

(58) Field of Classification Search .................. None
See application file for complete search history.

(56) References Cited

U.S. PATENT DOCUMENTS 7,053,268 B1   5/2006   Donaldson et al.

OTHER PUBLICATIONS

Bedell et al. (NCBI, Sequence Accession No. CW110126; Published Oct. 29, 2004).*
Kim et al., (Plant Molecular Biology, 24:105-117, 1994).
Benfey et al. (Science 250:959-966, 1990).

* cited by examiner

*Primary Examiner* — Vinod Kumar
(74) *Attorney, Agent, or Firm* — Kathryn K. Lappegard; Pioneer Hi-Bred International, Inc.

(57) ABSTRACT

The present invention provides compositions and methods for regulating expression of nucleotide sequences in a plant. Compositions are novel nucleotide sequences for a tissue preferred promoter isolated from the sorghum legumin coding region. The sequences drive expression preferentially to seed tissue, and most preferably to endosperm tissue of a plant. A method for expressing a nucleotide sequence in a plant using the regulatory sequences disclosed herein is provided. The method comprises transforming a plant cell to comprise a nucleotide sequence operably linked to one or more of the regulatory sequences of the present invention and regenerating a stably transformed plant from the transformed plant cell.

8 Claims, No Drawings

```
                        SEQUENCE LISTING

<160> NUMBER OF SEQ ID NOS: 8

<210> SEQ ID NO 1
<211> LENGTH: 818
<212> TYPE: DNA
<213> ORGANISM: Sorghum bicolor
<220> FEATURE:
<221> NAME/KEY: promoter
<222> LOCATION: (0)...(0)

<400> SEQUENCE: 1
tagctagctt ttctaaatat attaattttt gttatgcatg catctagaca tgcatggcgc      60
ataataacta agtgcattgc aaaaactata aatttagaaa aaccgaaata ttttataata     120
tagaattgag ggagtattag ttaggctatg cctccttatc atttcgttga tgatctagag     180
tactctagct atccccaaga gtaggccgga tggcggcacg gccacgaaat ttgtaggtga     240
aaacatgtag cagtgttaga gaagagtagg cagatcgcac aatgcaaatg cacctggaca     300
gtcgtacgtg cgtgtatata tgtaaactaa aggcgcaaca aactgttgga gtcagtacaa     360
aactgaatcg gcctttctga ctgtcagcac aagcaacaag tcgaagcgat cgatcatcca     420
cgtcgatctc taatgctggt taatcaagtt tgttagctag atacaaatgt attatttggc     480
atatatgtgt aaaaatgcat gtaacaccag cgagttacat gtctaacttg tcatattccc     540
aaccaacact cttatcacag caaagcaagc actagctagc atacaaaaga caaggcctga     600
atttgttcag aggtgccaca cttttttctt gcatcttttc atttcatatc attccttta      660 gtttattccc atttattttt atttttctgg aacaccagca gcacattcct ttgctatata     720
taaaaaaaaa agaccccgga cgggcctctg ctagctagca ctgcacacac ggccggcaac     780
agcactctgt cagtgaagag agtgagtgag cagaagcc                             818

<210> SEQ ID NO 2
<211> LENGTH: 1000
<212> TYPE: DNA
<213> ORGANISM: Oryza sativa
<220> FEATURE:
<221> NAME/KEY: promoter
<222> LOCATION: (0)...(0)

<400> SEQUENCE: 2
gtcataatgt cattcatcaa acttgtagct tgacaatgta cgtatatata gagggagaga      60
tatgagatat gatgaatcga atttgaagat gctcggcata cccggagcat gtctaggcaa     120
gctgttgtcc ggcctggaca tttctataat tactaaaact tgaaaaaaaa atccaggaag     180
atattaggca tttgtcattt tgccccctat gttcaatttt tgtgggttgt tagtttataa     240
aaatatgcat agtttatcaa gatgggactg taatctccaa gcttgggatg agcagcatat     300
atattgtgat ggttgatagc atatggctta tctcataatt catgacatca caaactattg     360
ggtaaaggca ttataatagg ttatagcaac aaatataaaa ttatgcttag ctgtgcaaaa     420
ttatctaatt gatgactatt tctaaataca catcatgggc aaaaaggtgc gaaaagttag     480
```

-continued

```
tggcagagta cataaatttg aaaagaatta taagtagttc cgtactcgac ataatacaaa      540
actaaaatat tcacacattt catctccgtt actttatgcg gtgtataaca tgagtgtaca      600
agctagacaa aaatgacaac aaaaatacaa cttttttgtt gtaaaagaaa aacaaactta      660
tcccatgcag aaactttatg acgcaggcac aaataaagcc aagaaggaaa aacatctaaa      720
gtgtagggat agaaaatttc tgaactaaaa gaatatgcat ttttctacaa aacacaataa      780
aagcctagta tacatataga tgtcttgtta accgactttg tgtatatata cttttttttt      840
tgcacaactc aatacacttt ataggatgtc tattgtttat actccaagta actttgtaac      900
tgccttacat tccaagcggc tttttcttgg ctataaaagg gacctcatgt cttgggaaat      960
cacatcagtt gagtttccat tatcctttca ataaatagcc                          1000
```

<210> SEQ ID NO 3
<211> LENGTH: 1073
<212> TYPE: DNA
<213> ORGANISM: Zea mays
<220> FEATURE:
<221> NAME/KEY: promoter
<222> LOCATION: (0)...(0)

<400> SEQUENCE: 3

```
atcgagtcag gtcaacttgg ccaaacttaa actgtctcgg ctcgatatat taaggaaccg       60
aataagagaa ccaactcgtc tcatttgtga gttcgagctc tcccgagcta aaaaaacaat      120
atacacatat ataaaatagt ataaccaatt attagttaat tctagaccta tttaacacta      180 aaaagagta acaatactca cactttcaca tatcatgtca atataacacc aaattaacaa      240
atcacttatt aattcatcca acacaagtgc gwgatttgtt tttctgacaa atggttgctc      300
attcaagcta aagagctgac tcgaacacag ctcgagctgg cttgttaaca aatcttgctg      360
agatactagc tcagctcgtg acaaaatcaa aatgagctga gctgaattga gtcgagctaa      420
ccatgaaccg agcgatctca cgagccacga gtattttgtc tagtcytacc aaaaagaccg      480
gtccattctt ctagtactag tccgaacccc gaaaacttta tgatttccat agcatttgtc      540
aaggctgcct cattaatcat tttgttgacg atctagagta ctctagcgaa acatgcaag       600 caaccaaacc gtagagaagt gtagtaggca aggctggtcg ctaatgcgtg cacctggaca      660
gtcgtaatcg gactgtgcgt gaacgaacta aaaaggcgca acaaactgtt ggagtcgyta      720
gtcagtacaa aactgaagcg gcctttgccc ttttgtgact gtcagcacaa gcaacaagtc      780
caaactgttg agcacacgat ccatccaagt cgacatccta ctgctgatcg atcgcgagct      840
tgtcaggttc ttcccatcca acgtgcacag ctcctatcac ggcaaagcaa agcaccagca      900
gcgtacgagg acaaggcctg aatttgttcc caggtgcaac aaaacacttt tgttcttttt      960
agctttgcat ccttctcgtt ccacttactt aatggcacac catcagcaat gcacaccacg     1020
gcaacagcat tcactgccaa gagagtgagc gagcgagcag aggcagcgca gca            1073
```

<210> SEQ ID NO 4
<211> LENGTH: 494
<212> TYPE: DNA
<213> ORGANISM: Sorghum bicolor
<220> FEATURE:
<221> NAME/KEY: terminator
<222> LOCATION: (0)...(0)

-continued

<400> SEQUENCE: 4

```
gcacctgaga gtgatctacc tgaataagta ctcgtggact gtaataaaca aagcttgttc    60
atgggtaaac tgcatgtctg ctgcatggat gagtctttca actacatata tagctcgtca   120
aatagaacaa cttaacttaa gtgagtaatg tttcaaatga gaacttgtgt cagggaaaaa   180
atgagaactt gtgtcaggga aaccaattcc aagttccaac ttatctacat agatgtggca   240
attagtcact ctgtcacatg gggaaccaaa tattcaatag cagataacag agtacaaata   300
tatcgattca ccatctgaac caactactac ctacggttaa agcttgaaat tacccactgg   360
tgcattgatt tatagtttgc agaaactaaa agtataaga ccacaccaca tctatctaca   420
tgtccaactc caacctaaag gtcaatctcc atctggcgtt tcctcatcat cagtgttgtc   480
gcctatctaa gctt                                                    494
```

<210> SEQ ID NO 5
<211> LENGTH: 34
<212> TYPE: DNA
<213> ORGANISM: Artificial Sequence
<220> FEATURE:
<223> OTHER INFORMATION: SB-LEG1 promoter primer

<400> SEQUENCE: 5

```
cggaccgggt tacctagcta gcttttctaa atat                               34
```

<210> SEQ ID NO 6
<211> LENGTH: 30
<212> TYPE: DNA
<213> ORGANISM: Artificial Sequence
<220> FEATURE:
<223> OTHER INFORMATION: SB-LEG1 promoter primer

<400> SEQUENCE: 6

```
ccatggcttc tgctcactca ctctcttcac                                    30
```

<210> SEQ ID NO 7
<211> LENGTH: 38
<212> TYPE: DNA
<213> ORGANISM: Artificial Sequence
<220> FEATURE:
<223> OTHER INFORMATION: SB-LEG1 terminator PCR primer

<400> SEQUENCE: 7

```
ccatggcccg ggatccgcac ctgagagtga tctacctg                           38
```

<210> SEQ ID NO 8
<211> LENGTH: 40
<212> TYPE: DNA
<213> ORGANISM: Artificial Sequence
<220> FEATURE:
<223> OTHER INFORMATION: SB-LEG1 terminator PCR primer

<400> SEQUENCE: 8

```
cggaccgggt gaccaagctt agatatggcg acaacactga                         40
```

SEED-PREFERRED REGULATORY ELEMENTS

CROSS-REFERENCE PARAGRAPH

This application is a continuation of application U.S. Ser. No. 12/145,564, filed Jun. 25, 2008, now U.S. Pat. No. 7,622,637, which claims the benefit of U.S. Provisional Application No. 60/955,412, filed Aug. 13, 2007, which are herein incorporated by reference in their entirety.

FIELD OF THE INVENTION

The present invention relates to the field of plant molecular biology, more particularly to regulation of gene expression in plants.

BACKGROUND OF THE INVENTION

Expression of DNA sequences in a plant host is dependent upon the presence of operably linked regulatory elements that are functional within the plant host. Choice of the regulatory element will determine when and where within the organism the DNA sequence is expressed. Where continuous expression is desired throughout the cells of a plant, and/or throughout development, constitutive promoters are utilized. In contrast, where gene expression in response to a stimulus is desired, inducible promoters are the regulatory element of choice. Where expression in specific tissues or organs are desired, tissue-preferred promoters may be used. That is, they may drive expression in particular tissues or organs. Such tissue-preferred promoters may be temporally constitutive or inducible. With any of these variables, additional regulatory sequences upstream and/or downstream from a core promoter sequence may be included in expression constructs of transformation vectors to bring about varying levels of expression of nucleotide sequences in a transgenic plant.

As this field develops and more genes become accessible, a greater need exists for transformed plants with multiple genes. These multiple exogenous genes typically need to be controlled by separate regulatory sequences however. Further, some genes should be regulated constitutively whereas other genes should be expressed at certain developmental stages or locations in the transgenic organism. Accordingly, a variety of regulatory sequences having diverse effects is needed.

Diverse regulatory sequences are also needed as undesirable biochemical interactions can result from using the same regulatory sequence to control more than one gene. For example, transformation with multiple copies of a regulatory element may cause problems, such that expression of one or more genes may be affected.

Isolation and characterization of a promoter that can serve as a regulatory element for expression of isolated nucleotide sequences of interest in a constitutive manner are needed for impacting various traits in plants. The inventors have isolated just such a promoter.

SUMMARY OF THE INVENTION

The invention is directed to a promoter from a Sorghum bicolor legumin gene, useful as a regulatory region and providing for expression of an operably linked nucleotide sequence. In an embodiment the expression is driven in a seed-preferred manner. In further embodiments, the expression is driven in an endosperm-preferred manner. The invention is further directed to a terminator regulatory element from a Sorghum bicolor legumin gene, useful as a regulatory region and as a polyadenylation signal. The invention includes functional fragments of the promoter, which fragments retain the function of driving constitutive expression of an operably linked nucleotide sequences. Functional fragments of the terminator which retain polyadeylation signal function are also within the scope of the invention. Expression cassettes having the nucleotide sequence, plants expressing same, and methods of use in impacting expression of operably linked nucleotides sequences are within the scope of the invention.

DETAILED DESCRIPTION OF THE INVENTION

All references referred to are incorporated herein by reference.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

The seed of a plant includes a seed coat, the embryo, and a supply of stored food, the endosperm. The endosperm is comprised almost entirely of nutritional reserves, primarily of complex carbohydrate and insoluble protein. The principle tissue types in maize seeds are the embryo, the endosperm including a surrounding aleurone cell layer, and the maternally derived pericarp. Of these, the endosperm and to a lesser extent the embryo, comprise most of the volume of the seed. Endosperm promoters are of particular interest for modifying seed characteristics and contents.

In accordance with the invention, nucleotide sequences are provided that allow regulation of transcription in an endosperm-preferred manner. Thus, the compositions of the present invention comprise novel nucleotide sequences for plant regulatory elements natively associated with the nucleotide sequences coding for Sorghum bicolor legumin protein, identified here as SB-LEG.

In an embodiment, the regulatory element drives transcription in an endosperm-preferred manner, wherein said regulatory element comprises a nucleotide sequence selected from the group consisting of: a) sequences natively associated with, and that regulate expression of DNA coding for sorghum SB-LEG (Sorghum bicolor legumin protein); b) the sequence of SEQ ID NO: 1; c) a sequence comprising a functional fragment of the nucleotide sequence set forth in SEQ ID NO: 1; or d) the sequence of SEQ ID NO: 4.

Further embodiments are to expression cassettes, transformation vectors, plants, and plant cells comprising the above nucleotide sequences. The invention is further to methods of using the sequence in plants and plant cells.

A method for expressing an isolated nucleotide sequence in a plant using the regulatory sequences disclosed herein is provided. The method comprises transforming a plant cell with a transformation vector that comprises an isolated nucleotide sequence operably linked to one or more of the plant regulatory sequences of the present invention and regenerating a stably transformed plant from the transformed plant cell. In this manner, the regulatory sequences are useful for controlling the expression of endogenous as well as exogenous products in an endosperm tissue-preferred manner.

Alternatively, it might be desirable to inhibit expression of a native DNA sequence within a plant's tissues to achieve a desired phenotype. In this case, such inhibition might be accomplished, for example, with transformation of the plant to comprise the tissue-specific promoter operably linked to an antisense nucleotide sequence, hairpin, RNA interfering or other nucleic acid molecule, such that tissue-preferred expression of the molecule interferes with translation of the mRNA of the native DNA sequence or otherwise inhibits expression of same in a subset of the plant's cells.

Under the regulation of the regulatory element will be a sequence of interest, which will provide for modification of the phenotype of the plant. Such modification includes modulating the production of an endogenous product, as to amount, relative distribution, or the like, or production of an exogenous expression product to provide for a novel function or product in the plant. Such a promoter is useful for a variety of applications, such as production of transgenic plants and seed with desired seed traits, including, for example, altered oil content, protein quality, cell growth or nutrient quality.

By "tissue-preferred" or endosperm-preferred promoter is intended expression which is capable of transcribing an operatively linked nucleotide sequence efficiently and expressing said sequence at higher levels in the described tissues, here the endosperm cells, than in other cells of the plant. Tissue can refer to a cell of a particular tissue.

By "regulatory element" is intended sequences responsible for expression of the linked nucleic acid molecule including, but not limited to, promoters, terminators, enhancers, introns, and the like.

By "promoter" is intended a regulatory region of DNA capable of regulating the transcription of a sequence linked thereto. It usually comprises a TATA box capable of directing RNA polymerase II to initiate RNA synthesis at the appropriate transcription initiation site for a particular coding sequence.

A promoter may additionally comprise other recognition sequences generally positioned upstream or 5' to the TATA box, referred to as upstream promoter elements, which influence the transcription initiation rate and further include elements which impact spatial and temporal expression of the linked nucleotide sequence. It is recognized that having identified the nucleotide sequences for the promoter region disclosed herein, it is within the state of the art to isolate and identify further regulatory elements in the 5' region upstream from the particular promoter region. Thus the promoter region disclosed here may comprise upstream regulatory elements such as those responsible for tissue and temporal expression of the nucleic acid molecule, and may include enhancers, the DNA response element for a transcriptional regulatory protein, ribosomal binding sites, transcriptional start and stop sequences, translational start and stop sequences, activator sequence and the like.

In the same manner, the promoter elements which enable such expression can be identified, isolated, and used with other core promoters to confirm seed-preferred expression or endosperm-preferred expression. By core promoter is meant the minimal sequence required to initiate transcription, such as the sequence called the TATA box which is common to promoters in genes encoding proteins. Thus the upstream promoter of SB-LEG can optionally be used in conjunction with its own or core promoters from other sources. The promoter may be native or non-native to the cell in which it is found.

The isolated promoter sequence of the present invention can be modified to provide for a range of expression levels of the isolated nucleotide sequence. Less than the entire promoter region can be utilized and the ability to drive tissue preferred expression retained. It is recognized that expression levels of mRNA can be modulated with specific deletions of portions of the promoter sequence. Thus, the promoter can be modified to be a weak or strong promoter. Generally, by "weak promoter" is intended a promoter that drives expression of a coding sequence at a low level. By "low level" is intended levels of about $1/10,000$ transcripts to about $1/100,000$ transcripts to about $1/500,000$ transcripts. Conversely, a strong promoter drives expression of a coding sequence at a high level, or at about $1/10$ transcripts to about $1/100$ transcripts to about $1/1,000$ transcripts. Generally, at least about 20 nucleotides of an isolated promoter sequence will be used to drive expression of a nucleotide sequence.

It is recognized that to increase transcription levels enhancers can be utilized in combination with the promoter regions of the invention. Enhancers are nucleotide sequences that act to increase the expression of a promoter region. Enhancers are known in the art and include the SV40 enhancer region, the 35S enhancer element, and the like.

The promoter of the present invention can be isolated from the 5' region of its native coding region or 5' untranslated region (5' UTR). Likewise the terminator can be isolated from the 3' region flanking its respective stop codon.

The term "isolated" refers to material, such as a nucleic acid or protein, which is: (1) substantially or essentially free from components which normally accompany or interact with the material as found in its naturally occurring environment, or (2) if the material is in its natural environment, the material has been altered by deliberate human intervention to a composition and/or placed at a locus in a cell other than the locus native to the material. Methods for isolation of promoter regions are well known in the art. One method is the use of primers and genomic DNA used in conjunction with the Genome Walker Kit™ (Clonetech).

The SB-LEG promoter set forth in SEQ ID NO:1 is 818 base pair nucleotides in length. The SB-LEG promoter was isolated from the *Sorghum bicolor* SB-LEG coding region. It was isolated based on sequence assembled from the publicly available Genome Survey Sequence (GSS).

The regulatory regions of the invention may be isolated from any plant, including, but not limited to sorghum (*Sorghum bicolor, Sorghum vulgare*), corn (*Zea mays*), canola (*Brassica napus, Brassica rapa* ssp.), alfalfa (*Medicago sativa*), rice (*Oryza sativa*), rye (*Secale cereale*), sunflower (*Helianthus annuus*), wheat (*Triticum aestivum*), soybean (*Glycine max*), tobacco (*Nicotiana tabacum*), millet (*Panicum* spp.), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats (*Avena sativa*), barley (*Hordeum vulgare*), vegetables, ornamentals, and conifers. Preferably, plants include corn, soybean, sunflower, safflower, canola, wheat, barley, rye, alfalfa, and sorghum.

Promoters isolated from one plant species can be expected to express in another plant species. For example, maize promoters have been used repeatedly to drive expression of genes in non-maize plants, including tobacco (Yang et al. (1990) "Maize sucrose synthase-1 promoter drives phloem cell-specific expression of GUS gene in transgenic tobacco plants" *Proc. Natl. Acad. Sci. USA* 87:4144-4148; Geffers et al., (2000) "Anaerobiosis-specific interaction of tobacco nuclear factors with cis-regulatory sequences in the maize GapC4 promoter" *Plant Mol. Biol.* 43:11-21); cultured rice cells (Vilardell et al., (1991) "Regulation of the maize rab 17 gene promoter in transgenic heterologous systems" *Plant Mol. Biol.* 17:985-993), wheat (Oldach et al., (2001) "Heterologous expression of genes mediating enhanced fungal resistance in transgenic wheat" *Mol. Plant. Microbe Interact.* 14:832-838; Brinch-Pedersen et al., (2003) "Concerted action of endogenous and heterologous phytase on phytic acid degradation in seed of transgenic wheat (*Triticum aestivum* L.)" *Transgenic Res.* 12:649-659), rice (Cornejo et al., (1993) "Activity of a maize ubiquitin promoter in transgenic rice" *Plant Mol. Biol.* 23:567-581; Takimoto et al., (1994) "Non-systemic expression of a stress-response maize polyubiquitin gene (Ubi-1) in transgenic rice plants" *Plant Mol. Biol.* 26:1007-1012), sunflower (Roussell et al., (1988) "Deletion of DNA sequences flanking an Mr 19,000 zein gene reduces its transcriptional activity in heterologous plant tissues" *Mol. Gen. Genet.* 211:202-209), and protoplasts of carrot (Roussell et al., 1988).

Regulatory sequences from other plants may be isolated according to well-known techniques based on their sequence homology to the coding region of the sequences set forth herein. In these techniques, all or part of the known coding sequence is used as a probe which selectively hybridizes to other sequences present in a population of cloned genomic DNA fragments (i.e. genomic libraries) from a chosen organism. Methods are readily available in the art for the hybridization of nucleic acid sequences. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995).

"Functional variants" of the regulatory sequences are also encompassed by the compositions of the present invention. Functional variants include, for example, the native regulatory sequences of the invention having one or more nucleotide substitutions, deletions or insertions. Functional variants of the invention may be created by site-directed mutagenesis, induced mutation, or may occur as allelic variants (polymorphisms).

As used herein, a "functional fragment" is a regulatory sequence variant formed by one or more deletions from a larger regulatory element. For example, the 5' portion of a promoter up to the TATA box near the transcription start site can be deleted without abolishing promoter activity, as described by Opsahl-Sorteberg et al., "Identification of a 49-bp fragment of the HvLTP2 promoter directing aleruone cell specific expression" *Gene* 341:49-58 (2004). Such fragments should retain promoter activity, particularly the ability to drive expression in the select tissue. Activity can be measured by Northern blot analysis, reporter activity measurements when using transcriptional fusions, and the like. See, for example, Sambrook et al. (1989) *Molecular Cloning: A Laboratory Manual* (2nd ed. Cold Spring Harbor Laboratory, Cold Spring Harbor, N.Y.).

Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology See particularly, Mullis et al. (1987) *Methods Enzymol.* 155:335-350, and Erlich, ed. (1989) *PCR Technology* (Stockton Press, New York).

For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3',4-base overhangs. Timed digests of a clone with this enzyme produces unidirectional nested deletions.

The entire promoter sequence or portions thereof can be used as a probe capable of specifically hybridizing to corresponding promoter sequences. To achieve specific hybridization under a variety of conditions, such probes include sequences that are unique and are preferably at least about 10 nucleotides in length, and most preferably at least about 20 nucleotides in length. Such probes can be used to amplify corresponding promoter sequences from a chosen organism by the well-known process of polymerase chain reaction (PCR). This technique can be used to isolate additional promoter sequences from a desired organism or as a diagnostic assay to determine the presence of the promoter sequence in an organism. Examples include hybridization screening of plated DNA libraries (either plaques or colonies; see e.g. Innis et al. (1990) *PCR Protocols, A Guide to Methods and Applications*, eds., Academic Press). Primers used in isolating the promoter of the present invention are shown below.

In referring to a terminator sequence is meant a nucleotide sequence that functions as a polyadenylation signal and signals the end of transcription. Functional fragments which retain such activity are within the scope of the invention.

The regulatory elements disclosed in the present invention, as well as variants and fragments thereof, are useful in the genetic manipulation of any plant when operably linked with an isolated nucleotide sequence of interest whose expression is to be controlled to achieve a desired phenotypic response.

By "operably linked" is intended a functional linkage between a regulatory region and a second sequence, wherein the regulatory sequence initiates and mediates transcription of the DNA sequence corresponding to the second sequence.

The regulatory elements of the invention can be operably linked to the isolated nucleotide sequence of interest in any of several ways known to one of skill in the art. The isolated nucleotide sequence of interest can be inserted into a site within the genome which is 3' to the promoter of the invention using site specific integration as described in U.S. Pat. No. 6,187,994. The term "nucleotide sequence of interest" refers to a nucleic acid molecule (which may also be referred to as a polynucleotide) which can be an RNA molecule as well as DNA molecule, and can be a molecule that encodes for a desired polypeptide or protein, but also may refer to nucleic acid molecules that do not constitute an entire gene, and which do not necessarily encode a polypeptide or protein. For example, when used in a homologous recombination process, the promoter may be placed in a construct with a sequence that targets an area of the chromosome in the plant but may not encode a protein. If desired, the nucleotide sequence of interest can be optimized for plant translation by optimizing the codons used for plants and the sequence around the translational start site for plants. Sequences resulting in potential mRNA instability can also be avoided.

The regulatory elements of the invention can be operably linked in expression cassettes along with isolated nucleotide sequences of interest for expression in the desired plant. Such an expression cassette is provided with a plurality of restriction sites for insertion of the nucleotide sequence of interest under the transcriptional control of the regulatory elements.

Alternatively, a specific result can be achieved by providing for a reduction of expression of one or more endogenous products, particularly enzymes or cofactors in the plant. This down regulation can be achieved through many different approaches known to one skilled in the art, including antisense, co-suppression, use of hairpin formations, or others, and discussed infra. Importation or exportation of a cofactor also allows for control of plant composition. It is recognized that the regulatory elements may be used with their native or other coding sequences to increase or decrease expression of an operably linked sequence in the transformed plant or seed.

General categories of genes of interest for the purposes of the present invention include for example, those genes involved in information, such as zinc fingers; those involved in communication, such as kinases; and those involved in housekeeping, such as heat shock proteins. More specific categories of transgenes include genes encoding important traits for agronomics, insect resistance, disease resistance, herbicide resistance, and grain characteristics. Still other categories of transgenes include genes for inducing expression of exogenous products such as enzymes, cofactors, and hormones from plants and other eukaryotes as well as prokaryotic organisms.

Modifications that affect grain traits include increasing the content of oleic acid, or altering levels of saturated and unsaturated fatty acids. Likewise, the level of plant proteins, particularly modified proteins that improve the nutrient value of the plant, can be increased. This is achieved by the expression of such proteins having enhanced amino acid content.

Increasing the levels of lysine and sulfur-containing amino acids may be desired as well as the modification of starch type and content in the seed. Hordothionin protein modifications are described in WO 9416078 filed Apr. 10, 1997; WO 9638562 filed Mar. 26, 1997; WO 9638563 filed Mar. 26, 1997 and U.S. Pat. No. 5,703,409 issued Dec. 30, 1997. Another example is lysine and/or sulfur-rich plant protein encoded by the soybean 2S albumin described in WO 9735023 filed Mar. 20, 1996, and the chymotrypsin inhibitor from barley, Williamson et al. (1987) *Eur. J. Biochem.* 165: 99-106.

Agronomic traits in plants can be improved by altering expression of genes that: affect the response of plant growth and development during environmental stress, Cheikh-N et al. (1994) *Plant Physiol.* 106(1):45-51) and genes controlling carbohydrate metabolism to reduce kernel abortion in maize, Zinselmeier et al. (1995) *Plant Physiol.* 107(2):385-391.

It is recognized that any nucleotide sequence of interest, including the native coding sequence, can be operably linked to the regulatory elements of the invention and expressed in the plant.

Commercial traits in plants can be created through the expression of genes that alter starch or protein for the production of paper, textiles, ethanol, polymers or other materials with industrial uses.

Means for increasing or inhibiting a protein are well known to those skilled in the art and, include, but are not limited to: transgenic expression, antisense suppression, co-suppression, RNA interference, gene activation or suppression using transcription factors and/or repressors; mutagenesis including, but not limited to, transposon tagging; directed and site-specific mutagenesis, chromosome engineering (see Nobrega et. al., *Nature* 431:988-993(04)), homologous recombination, TILLING (Targeting Induced Local Lesions In Genomes), and biosynthetic competition to manipulate the expression of proteins. Many techniques for gene silencing are well known to one of skill in the art, including but not limited to knock-outs (such as by insertion of a transposable element such as Mu, Vicki Chandler, *The Maize Handbook* ch. 118 (Springer-Verlag 1994) or other genetic elements such as a FRT, Lox or other site specific integration site; RNA interference (Napoli et al. (1990) *Plant Cell* 2:279-289; U.S. Pat. No. 5,034,323, Sharp (1999) *Genes Dev.* 13:139-141, Zamore et al. (2000) *Cell* 101:25-33; and Montgomery et al. (1998) *PNAS USA* 95:15502-15507); virus-induced gene silencing (Burton et al. (2000) *Plant Cell* 12:691-705, and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407: 319-320; WO 99/53050; and WO 98/53083); MicroRNA (Aukerman & Sakai (2003) *Plant Cell* 15:2730-2741); ribozymes (Steinecke et al. (1992) *EMBO J.* 11:1525, and Perriman et al. (1993) *Antisense Res. Dev.* 3:253); oligonucleotide mediated targeted modification (e.g., WO 03/076574 and WO 99/25853); zinc-finger targeted molecules (e.g., WO 01/52620; WO 03/048345; and WO 00/42219); and other methods or combinations of the above methods known to those of skill in the art.

The nucleotide sequence operably linked to the regulatory elements disclosed herein can be an antisense sequence for a targeted gene. (See, e.g., Sheehy et al. (1988) *PNAS USA* 85:8805-8809; and U.S. Pat. Nos. 5,107,065; 5,453,566; and 5,759,829). By "antisense DNA nucleotide sequence" is intended a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing with the endogenous messenger RNA (mRNA) produced by transcription of the DNA nucleotide sequence for the targeted gene. In this case, production of the native protein encoded by the targeted gene is inhibited to achieve a desired phenotypic response. Thus the regulatory sequences disclosed herein can be operably linked to antisense DNA sequences to reduce or inhibit expression of a native protein in the plant.

As noted, other potential approaches to impact expression of proteins in the plant include traditional co-suppression, that is, inhibition of expression of an endogenous gene through the expression of an identical structural gene or gene fragment introduced through transformation (Goring, D. R., Thomson, L., Rothstein, S. J. 1991. *Proc. Natl. Acad. Sci. USA* 88:1770-1774 co-suppression; Taylor (1997) *Plant Cell* 9:1245; Jorgensen (1990) *Trends Biotech.* 8(12):340-344; Flavell (1994) *PNAS USA* 91:3490-3496; Finnegan et al. (1994) *Bio/Technology* 12:883-888; and Neuhuber et al. (1994) *Mol. Gen. Genet.* 244:230-241)). In one example, co-suppression can be achieved by linking the promoter to a DNA segment such that transcripts of the segment are produced in the sense orientation and where the transcripts have at least 65% sequence identity to transcripts of the endogenous gene of interest, thereby suppressing expression of the endogenous gene in said plant cell. (See, U.S. Pat. No. 5,283, 184). The endogenous gene targeted for co-suppression may be a gene encoding any protein that accumulates in the plant species of interest. For example, where the endogenous gene targeted for co-suppression is the 50 kD gamma-zein gene, co-suppression is achieved using an expression cassette comprising the 50 kD gamma-zein gene sequence, or variant or fragment thereof.

Additional methods of down-regulation are known in the art and can be similarly applied to the instant invention. These methods involve the silencing of a targeted gene by spliced hairpin RNA's and similar methods also called RNA interference and promoter silencing (see Smith et al. (2000) *Nature* 407:319-320, Waterhouse and Helliwell (2003)) *Nat. Rev. Genet.* 4:29-38; Waterhouse et al. (1998) *Proc. Natl. Acad. Sci. USA* 95:13959-13964; Chuang and Meyerowitz (2000) *Proc. Natl. Acad. Sci. USA* 97:4985-4990; Stoutjesdijk et al. (2002) *Plant Phystiol.* 129:1723-1731; and Patent Application WO 99/53050; WO 99/49029; WO 99/61631; WO 00/49035 and U.S. Pat. No. 6,506,559.

For mRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). miRNA molecules are highly efficient at inhibiting the expression of endogenous genes, and the RNA interference they induce is inherited by subsequent generations of plants.

In one embodiment, the polynucleotide to be introduced into the plant comprises an inhibitory sequence that encodes a zinc finger protein that binds to a gene encoding a protein of the invention resulting in reduced expression of the gene. In particular embodiments, the zinc finger protein binds to a regulatory region of a gene of the invention. In other embodiments, the zinc finger protein binds to a messenger RNA encoding a protein and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication No. 2003/0037355.

The regulatory region of the invention may also be used in conjunction with another promoter. In one embodiment, the plant selection marker and the gene of interest can be both functionally linked to the same promoter. In another embodiment, the plant selection marker and the gene of interest can be functionally linked to different promoters. In yet other embodiments, the expression vector can contain two or more genes of interest that can be linked to the same promoter or different promoters. For example, the SB-LEG promoter described here can be used to drive the gene of interest and the selectable marker, or a different promoter used for one or the other. These other promoter elements can be those that are constitutive or sufficient to render promoter-dependent gene expression controllable as being cell-type specific, tissue-specific or time or developmental stage specific, or being inducible by external signals or agents. Such elements may be located in the 5' or 3' regions of the gene. Although the additional promoter may be the endogenous promoter of a structural gene of interest, the promoter can also be a foreign regulatory sequence. Promoter elements employed to control expression of product proteins and the selection gene can be any plant-compatible promoters. These can be plant gene promoters, such as, for example, the ubiquitin promoter (Christensen et al. (1989) *Plant Mol. Biol.* 12:619-632 and Christensen et al. (1992) *Plant Mol. Biol.* 18:675-689); the promoter for the small subunit of ribulose-1,5-bis-phosphate carboxylase (ssRUBISCO) (Coruzzi et al., 1984; Broglie et al., 1984); or promoters from the tumor-inducing plasmids from *Agrobacterium tumefaciens*, such as the nopaline synthase, octopine synthase and mannopine synthase promoters (Velten, J. and Schell, J. (1985) "Selection-expression plasmid vectors for use in genetic transformation of higher plants" *Nucleic Acids Res.* 13:6981-6998; Depicker et al., (1982) *Mol. and Appl. Genet.* 1:561-573 Shaw et al. (1984) *Nucleic Acids Research* vol. 12, No. 20 pp. 7831-7846) that have plant activity; or viral promoters such as the cauliflower mosaic virus (CaMV) 19S and 35S promoters (Guilley et al. (1982) "Transcription of Cauliflower mosaic virus DNA: detection of promoter sequences, and characterization of transcripts" *Cell* 30:763-773.; Odell et al. (1985) "Identification of DNA sequences required for activity of the cauliflower mosaic virus 35S promoter" *Nature* 313:810-812, the figwort mosaic virus FLt promoter (Maiti et al. (1997) "Promoter/leader deletion analysis and plant expression vectors with the figwort mosaic virus (FMV) full length transcript (FLt) promoter containing single or double enhancer domains" *Transgenic Res.* 6:143-156) or the coat protein promoter of TMV (Grdzelishvili et al., 2000) "Mapping of the tobacco mosaic virus movement protein and coat protein subgenomic RNA promoters in vivo" *Virology* 275:177-192).

The expression cassette may also include at the 3' terminus of the isolated nucleotide sequence of interest, a transcriptional and translational termination region functional in plants. The termination region can be native with the promoter nucleotide sequence of the present invention, can be native with the DNA sequence of interest, or can be derived from another source. Thus, any convenient termination regions can be used in conjunction with the promoter of the invention, and are available from the Ti-plasmid of *A. tumefaciens*, such as the octopine synthase and nopaline synthase termination regions. See also: Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. 1989) *Nucleic Acids Res.* 17:7891-7903; Joshi et al. (1987) *Nucleic Acid Res.* 15:9627-9639.

The expression cassettes can additionally contain 5' leader sequences. Such leader sequences can act to enhance translation. Translation leaders are known in the art and include: picornavirus leaders, for example, EMCV leader (Encephalomyocarditis 5' noncoding region), Elroy-Stein et al. (1989) *Proc. Natl. Acad. Sci. USA* 86:6126-6130; potyvirus leaders, for example, TEV leader (Tobacco Etch Virus), Allison et al. (1986); MDMV leader (Maize Dwarf Mosaic Virus), *Virology* 154:9-20; human immunoglobulin heavy-chain binding protein (BiP), Macejak et al. (1991) *Nature* 353:90-94; untranslated leader from the coat protein mRNA of alfalfa mosaic virus (AMV RNA 4), Jobling et al. (1987) *Nature* 325:622-625); tobacco mosaic virus leader (TMV), Gallie et al (1989) *Molecular Biology of RNA*, pages 237-256; and maize chlorotic mottle virus leader (MCMV), Lommel et al. (1991) *Virology* 81:382-385. See also Della-Cioppa et al. (1987) *Plant Physiology* 84:965-968. The cassette can also contain sequences that enhance translation and/or mRNA stability such as introns.

In those instances where it is desirable to have an expressed product of an isolated nucleotide sequence directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to: the transit peptide for the acyl carrier protein, the small subunit of RUBISCO, plant EPSP synthase, and the like.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations can be involved to provide for convenient restriction sites, removal of superfluous DNA, removal of restriction sites, or the like. For this purpose, in vitro mutagenesis, primer repair, restriction digests, annealing, and resubstitutions such as transitions and transversions, can be involved.

Reporter genes can be included in the transformation vectors. Examples of suitable reporter genes known in the art can be found in, for example: Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et al. (1990) EMBO J. 9:2517-2522; Kain et al. (1995) *BioTechniques* 19:650-655; and Chiu et al. (1996) *Current Biology* 6:325-330.

Selectable marker genes for selection of transformed cells or tissues can be included in the transformation vectors. These can include genes that confer antibiotic resistance or resistance to herbicides. Examples of suitable selectable marker genes include, but are not limited to: genes encoding resistance to chloramphenicol, Herrera Estrella et al. (1983) *EMBO J.* 2:987-992; methotrexate, Herrera Estrella et al. (1983) *Nature* 303:209-213; Meijer et al. (1991) *Plant Mol. Biol.* 16:807-820; hygromycin, Waldron et al. (1985) *Plant Mol. Biol.* 5:103-108; Zhijian et al. (1995) *Plant Science* 108:219-227; streptomycin, Jones et al. (1987) *Mol. Gen. Genet.* 210:86-91; spectinomycin, Bretagne-Sagnard et al. (1996) *Transgenic Res.* 5:131-137; bleomycin, Hille et al. (1990) *Plant Mol. Biol.* 7:171-176; sulfonamide, Guerineau et al. (1990) *Plant Mol. Biol.* 15:127-136; bromoxynil, Stalker et al. (1988) *Science* 242:419-423; glyphosate, Shaw et al. (1986) *Science* 233:478-481; phosphinothricin, DeBlock et al. (1987) *EMBO J.* 6:2513-2518 including the maize optimized "pat" gene., Gordon-Kamm (1990) *The Plant Cell* 2: 603; Uchimiya et al. (1993) Bio/Technology 11: 835; and Anzai et al. (1989) *Mol. Gen. Gen.* 219:492).

Further, when linking a promoter of the invention with a nucleotide sequence encoding a detectable protein, expression of a linked sequence can be tracked in the plant, thereby providing useful screenable or scorable markers. The expression of the linked protein can be detected without the necessity of destroying tissue. By way of example without limitation, the promoter can be linked with detectable markers including a β-glucuronidase, or uidA gene (GUS), which encodes an enzyme for which various chromogenic substrates are known (Jefferson et al., 1986, *Proc. Natl. Acad. Sci. USA* 83:8447-8451); chloramphenicol acetyl transferase; alkaline phosphatase; a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988); Ludwig et al. (1990) *Science* 247:449); a p-lactamase gene (Sutcliffe, *Proc. Nat'l. Acad. Sci. U.S.A.* 75:3737 (1978)), which encodes an enzyme for which various chromogenic substrates are known (e.g., PADAC, a chromogenic cephalosporin); a xylE gene (Zukowsky et al., *Proc. Nat'l. Acad. Sci. U.S.A.* 80:1101 (1983)), which encodes a catechol dioxygenase that can convert chromogenic catechols; an α-amylase gene (Ikuta et al., *Biotech.* 8:241 (1990)); a tyrosinase gene (Katz et al., *J. Gen. Microbiol.* 129:2703 (1983)), which encodes an enzyme capable of oxidizing tyrosine to DOPA and dopaquinone, which in turn condenses to form the easily detectable compound melanin a green fluorescent protein (GFP) gene (Sheen et al., *Plant J.* 8(5):777-84 (1995)); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) *EMBO J.* 8:343); DS-RED EXPRESS (Matz et al. (1999) *Nature Biotech.* 17:969-973, Bevis et al. (2002) *Nature Biotech* 20:83-87, Haas et al. (1996) *Curr. Biol.* 6:315-324); *Zoanthus* sp. yellow fluorescent protein (ZsYellow) that has been engineered for brighter fluorescence (Matz et al. (1999) *Nature Biotech.* 17:969-973, available from BD Biosciences Clontech, Palo Alto, Calif., USA, catalog no. 632443); and cyan florescent protein (CYP) (Bolte et al. (2004) *J. Cell Science* 117:943-54 and Kato et al. (2002) *Plant Physiol* 129:913-42).

As noted herein, the present invention provides vectors capable of expressing genes of interest under the control of the regulatory elements. In general, the vectors should be functional in plant cells. At times, it may be preferable to have vectors that are functional in *E. coli* (e.g., production of protein for raising antibodies, DNA sequence analysis, construction of inserts, obtaining quantities of nucleic acids). Vectors and procedures for cloning and expression in *E. coli* are discussed in Sambrook et al. (supra). The transformation vector comprising the regulatory sequence of the present invention operably linked to an isolated nucleotide sequence in an expression cassette, can also contain at least one additional nucleotide sequence for a gene to be co-transformed into the organism. Alternatively, the additional sequence(s) can be provided on another transformation vector. Vectors that are functional in plants can be binary plasmids derived from *Agrobacterium*. Such vectors are capable of transforming plant cells. These vectors contain left and right border sequences that are required for integration into the host (plant) chromosome. At minimum, between these border sequences is the gene to be expressed under control of the regulatory elements of the present invention. In one embodiment, a selectable marker and a reporter gene are also included.

A transformation vector comprising the particular regulatory sequences of the present invention, operably linked to an isolated nucleotide sequence of interest in an expression cassette, can be used to transform any plant. In this manner, genetically modified plants, plant cells, plant tissue, and the like can be obtained. Transformation protocols can vary depending on the type of plant or plant cell, i.e., monocot or dicot, targeted for transformation. Suitable methods of transforming plant cells include microinjection, Crossway et al. (1986) *Biotechniques* 4:320-334; electroporation, Riggs et al. (1986) *Proc. Natl. Acad. Sci. USA* 83:5602-5606; *Agrobacterium*-mediated transformation, see for example, Townsend et al. U.S. Pat. No. 5,563,055; direct gene transfer, Paszkowski et al. (1984) *EMBO J.* 3:2717-2722; and ballistic particle acceleration, see for example, Sanford et al. U.S. Pat. No. 4,945,050, Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6:923-926. Also see Weissinger et al. (1988) *Annual Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Datta et al. (1990) *Bio/Technology* 8:736-740 (rice); Klein et al. (1988) *Proc. Natl. Acad. Sci. USA* 85:4305-4309 (maize); Klein et al. (1988) *Biotechnology* 6:559-563 (maize); Klein et al. (1988) *Plant Physiol.* 91:440-444 (maize); Fromm et al. (1990) *Biotechnology* 8:833-839; Hooydaas-Van Slogteren et al. (1984) *Nature* (London) 311:763-764; Bytebier et al. (1987) *Proc. Natl. Acad. Sci. USA* 84:5345-5349 (Liliaceae); De Wet et al. (1985) in *The Experimental Manipulation of Ovule Tissues*, ed. G. P. Chapman et al. (Longman, New York), pp. 197-209 (pollen); Kaeppler et al. (1990) *Plant Cell Reports* 9:415-418; and Kaeppler et al. (1992) *Theor. Appl. Genet.* 84:560-566 (whisker-mediated transformation); Halluin et al. (1992) *Plant Cell* 4:1495-1505 (electroporation); Li et al. (1993) *Plant Cell Reports* 12:250-255 and Christou et al. (1995)

*Annals of Botany* 75:407-413 (rice); Osjoda et al. (1996) *Nature Biotechnology* 14:745-750 (maize via *Agrobacterium tumefaciens*).

The cells that have been transformed can be grown into plants in accordance with conventional methods. See, for example, McCormick et al. (1986) *Plant Cell Reports* 5:81-84. These plants can then be grown and pollinated with the same transformed strain or different strains. The resulting plant having constitutive expression of the desired phenotypic characteristic can then be identified. Two or more generations can be grown to ensure that constitutive expression of the desired phenotypic characteristic is stably maintained and inherited.

EXAMPLES

Example 1

Isolation of Regulatory Sequences

Regulatory regions from sorghum SB-LEG (*Sorghum bicolor* legumin) were isolated from sorghum plants and cloned. *Sorghum* SB-LEG was selected as a source of seed preferred regulatory elements based on the spatial and temporal expression of its products.

The promoter is an 818 base pair nucleotide sequence. A BLAST of GenBank showed the highest identity was 55% to the maize legumin promoter, described at Abbitt et al., U.S. Pat. No. 7,211,712.

Motifs were identified that were common to all three legumin promoters, thus indicating the importance of these regions. These include:

TTGTTA

AGAGTA

CAACAA

CTTTTT

The method for isolation of the above sequences is described below:

The SB-LEG1 Promoter and terminator were isolated using the sequences from the GSS database to choose primers for PCR. Primers used were:

```
SB-LEG1 PRO PCR Primers:
                                        (SEQ ID NO: 5)
TMS1575:  CGGACCGGGTTACCTAGCTAGCTTTTCTAAATAT
                                        (SEQ ID NO: 6)
TMS1576:  CCATGGCTTCTGCTCACTCACTCTCTTCAC SB-LEG TERM PCR Primers:
                                        (SEQ ID NO: 7)
TMS1647:  CCATGGCCCGGGATCCGCACCTGAGAGTGATCTACCTG
                                        (SEQ ID NO: 8
TMS1648:  CGGACCGGGTGACCAAGCTTAGATATGGCGACAACACTGA.
```

The PCR reaction was performed in a Bio-Rad icycler (Hercules, Calif.) thermal cycler using Hifidelity supermix (Cat. #10790-020, Life Technologies, Rockville Md.). The following cycle parameters were used: 94° C. for 2 seconds, followed by 30 cycles of 94° C. for 20 seconds, for 30 seconds, and 68° C. for 1 minute. Finally, the samples were held at 67° C. for 4 minutes and then at 4° C. until further analysis.

The PCR products were cloned into the (Promega™) pGEM-easy vector and sequenced using M13F and M13R primers. Upon sequence verification, they were given PHP numbers and archived.

Example 2

Expression Data Using SG-LEG Regulatory Sequences

A promoter::GUS::terminator fusion construct was prepared by the methods described below. All vectors were constructed using standard molecular biology techniques (Sambrook et al., Supra). The construct included the SB-LEG promoter and terminator and a selectable marker: SB-LEG PRO: GUSINT:SB-LEG Term.

A reporter gene and a selectable marker gene for gene expression and selection was inserted between the multiple cloning sites of the pBluescript cloning vector (Stratagene Inc., 11011 N. Torrey Pines Rd., La Jolla, Calif.). The reporter gene was the β-glucuronidase (GUS) gene (Jefferson et al., 1986, *Proc. Natl. Acad. Sci. USA* 83:8447-8451) into whose coding region was inserted the second intron from the potato ST-LS1 gene (Vancanneyt et al., Mol. Gen. Genet. 220:245-250, 1990), to produce GUSINT, in order to prevent expression of the gene in *Agrobacterium* (see Ohta et al., 1990, Plant Cell Physiol. 31(6):805-813. Successful subcloning was confirmed by restriction analysis.

The *Agrobacterium* transformation plasmids were constructed by inserting the GUS expression cassettes into a descendent plasmid of pSB11 which contained the MOPAT expression cassette (UBI:UBI INTRON:MOPAT:PinII) (including the maize optimized pat gene, supra, along with the ubiquitin promoter and intron, supra and pinII terminator) for selection. Both the GUS and MOPAT expression cassettes were located between the right and left T-DNA. The GUS cassette was inserted proximal to the right T-DNA border. The plasmid pSB11 was obtained from Japan Tobacco Inc. (Tokyo, Japan). The construction of pSB11 from pSB21 and the construction of pSB21 from starting vectors is described by Komari et al. (1996, Plant J. 10:165-174). The T-DNA of the plasmid was integrated into the superbinary plasmid pSB1 (Saito et al., EP 672 752 A1) by homologous recombination between the two plasmids. The plasmid pSB1 was also obtained from Japan Tobacco Inc.

Competent cells of the *Agrobacterium* strain LBA4404 harboring pSB1 were created using the protocol as described by Lin (1995) in Methods in Molecular Biology, ed. Nickoloff, J. A. (Humana Press, Totowa, N.J.). The plasmid containing the expression cassettes was electroporated into competent cells of the *Agrobacterium* strain LBA4404 harboring pSB1 to create the cointegrate plasmid in *Agrobacterium* using a BIO-RAD Micropulser (Cat #165-2100, Hercules, Calif.). Electroporation was performed by mixing 1 ul of plasmid DNA (~100 ng) with 20.mu.l of competent *Agrobacterium* cells in a 0.2 cm electrode gap cuvette (Cat #165-2086, BIO-RAD, Hercules, Calif.). Electroporation was performed using the EC2 setting, which delivers 2.5 kV to the cells. Successful recombination was verified by restriction analysis of the plasmid after transformation of the cointegrate plasmid back into *E. coli* DH5a cells.

Example 3

Transformation and Regeneration of Maize Callus Via *Agrobacterium* Preparation of *Agrobacterium* Suspension

*Agrobacterium* was streaked out from a –80.degree. frozen aliquot onto a plate containing PHI-L medium and cultured at 28° C. in the dark for 3 days. PHI-L media comprises 25 ml/l Stock Solution A, 25 ml/l Stock Solution B, 450.9 ml/l Stock Solution C and spectinomycin (Sigma Chemicals) added to a concentration of 50 mg/l in sterile ddH.sub.20 (stock solution A: K2HPO4 60.0 g/l, NaH2PO4 20.0 g/l, adjust pH to 7.0 w/KOH and autoclaved; stock solution B: NH4Cl 20.0 g/l, MgSO4.7H2O 6.0 g/l, KCl 3.0 g/l, CaCl2 0.20 g/l, FeSO4.7H2O 50.0 mg/l, autoclaved; stock solution C: glucose 5.56 g/l, agar 16.67 g/l (#A-7049, Sigma Chemicals, St. Louis, Mo.) and autoclaved). The plate can be stored at 4° C. and used usually for about 1 month. A single colony was picked from the master plate and streaked onto a plate containing PHI-M medium [yeast extract (Difco) 5.0 g/l; peptone (Difco) 10.0 g/l; NaCl 5.0 g/l; agar (Difco) 15.0 g/l; pH 6.8, containing 50 mg/L spectinomycin] and incubated at 28° C. in the dark for 2 days. Five ml of either PHI-A, [CHU(N6) basal salts (Sigma C-1416) 4.0 g/l, Eriksson's vitamin mix (1000.times., Sigma-1511) 1.0 ml/l; thiamine.HCl 0.5 mg/l (Sigma); 2,4-dichlorophenoxyacetic acid (2,4-D, Sigma) 1.5 mg/l; L-proline (Sigma) 0.69 g/l; sucrose (Mallinckrodt) 68.5 g/l; glucose (Mallinckrodt) 36.0 g/l; pH 5.2] for the PHI basic medium system, or PHI-I [MS salts (GIBCO BRL) 4.3 g/l; nicotinic acid (Sigma) 0.5 mg/l; pyridoxine.HCl (Sigma) 0.5 mg/l; thiamine.HCl 1.0 mg/l; myo-inositol (Sigma) 0.10 g/l; vitamin assay casamino acids (Difco Lab) 1 g/l; 2,4-D 1.5 mg/l; sucrose 68.50 g/l; glucose 36.0 g/l; adjust pH to 5.2 w/KOH and filter-sterilize] for the PHI combined medium system and 5 ml of 100 mM (3'-5'-Dimethoxy-4'-hydroxyacetophenone, Aldrich chemicals) were added to a 14 ml Falcon tube in a hood. About 3 full loops (5 mm loop size) *Agrobacterium* was collected from the plate and suspended in the tube, then the tube vortexed to make an even suspension. One ml of the suspension was transferred to a spectrophotometer tube and the OD of the suspension adjusted to 0.72 at 550 nm by adding either more *Agrobacterium* or more of the same suspension medium, for an *Agrobacterium* concentration of approximately 0.5.times.109 cfu/ml to 1.times.109 cfu/ml. The final *Agrobacterium* suspension was aliquoted into 2 ml microcentrifuge tubes, each containing 1 ml of the suspension. The suspensions were then used as soon as possible.

Embryo Isolation, Infection and Co-Cultivation:

About 2 ml of the same medium (here PHI-A or PHI-I) used for the 30 *Agrobacterium* suspension were added into a 2 ml microcentrifuge tube. Immature embryos were isolated from a sterilized ear with a sterile spatula (Baxter Scientific Products S1565) and dropped directly into the medium in the tube. A total of about 100 embryos were placed in the tube. The optimal size of the embryos was about 1.0-1.2 mm. The cap was then closed on the tube and the tube vortexed with a Vortex Mixer (Baxter Scientific Products S8223-1) for 5 sec. at maximum speed. The medium was removed and 2 ml of fresh medium were added and the vortexing repeated. All of the medium was drawn off and 1 ml of *Agrobacterium* suspension added to the embryos and the tube vortexed for 30 sec. The tube was allowed to stand for 5 min. in the hood. The suspension of *Agrobacterium* and embryos was poured into a Petri plate containing either PHI-B medium [CHU(N6) basal salts (Sigma C-1416) 4.0 g/l; Eriksson's vitamin mix (1000.times., Sigma-1511) 1.0 ml/l; thiamine.HCl 0.5 mg/l; 2,4-D 1.5 mg/l; L-proline 0.69 g/l; silver nitrate 0.85 mg/l; gelrite (Sigma) 3.0 g/l; sucrose 30.0 g/l; acetosyringone 100 mM; pH 5.8], for the PHI basic medium system, or PHI-J medium [MS Salts 4.3 g/l; nicotinic acid 0.50 mg/l; pyridoxine HCl 0.50 mg/l; thiamine.HCl 1.0 mg/l; myo-inositol 100.0 mg/l; 2,4-D 1.5 mg/l; sucrose 20.0 g/l; glucose 10.0 g/l; L-proline 0.70 g/l; MES (Sigma) 0.50 g/l; 8.0 g/l agar (Sigma A-7049, purified) and 100 mM acetosyringone with a final pH of 5.8 for the PHI combined medium system. Any embryos left in the tube were transferred to the plate using a sterile spatula. The *Agrobacterium* suspension was drawn off and the embryos placed axis side down on the media. The plate was sealed with Parafilm tape or Pylon Vegetative Combine Tape (product named "E.G.CUT" and is available in 18 mm.times.50 m sections; Kyowa Ltd., Japan) and incubated in the dark at 23-25° C. for about 3 days of co-cultivation.

Resting, Selection and Regeneration Steps:

For the resting step, all of the embryos were transferred to a new plate containing PHI-C medium [CHU(N6) basal salts (Sigma C-1416) 4.0 g/l; Eriksson's vitamin mix (1000× Sigma-1511) 1.0 ml/l; thiamine.HCl 0.5 mg/l; 2,4-D 1.5 mg/l; L-proline 0.69 g/l; sucrose 30.0 g/l; MES buffer (Sigma) 0.5 g/l; agar (Sigma A-7049, purified) 8.0 g/l; silver nitrate 0.85 mg/l; carbenicillin 100 mg/l; pH 5.8]. The plate was sealed with Parafilm or Pylon tape and incubated in the dark at 28° C. for 3-5 days.

Longer co-cultivation periods may compensate for the absence of a resting step since the resting step, like the co-cultivation step, provides a period of time for the embryo to be cultured in the absence of a selective agent. Those of ordinary skill in the art can readily test combinations of co-cultivation and resting times to optimize or improve the transformation.

For selection, all of the embryos were then transferred from the PHI-C medium to new plates containing PHI-D medium, as a selection medium, [CHU(N6) basal salts (SIGMA C-1416) 4.0 g/l; Eriksson's vitamin mix (1000.times., Sigma-1511) 1.0 ml/l; thiamine.HCl 0.5 mg/l; 2,4-D 1.5 mg/l; L-proline 0.69 g/l; sucrose 30.0 g/l; MES buffer 0.5 g/l; agar (Sigma A-7049, purified) 8.0 g/l; silver nitrate 0.85 mg/l; carbenicillin (ICN, Costa Mesa, Calif.) 100 mg/l; bialaphos (Meiji Seika K.K., Tokyo, Japan) 1.5 mg/l for the first two weeks followed by 3 mg/l for the remainder of the time.; pH 5.8] putting about 20 embryos onto each plate.

The plates were sealed as described above and incubated in the dark at 28° C. for the first two weeks of selection. The embryos were transferred to fresh selection medium at two-week intervals. The tissue was subcultured by transferring to fresh selection medium for a total of about 2 months. The herbicide-resistant calli were then "bulked up" by growing on the same medium for another two weeks until the diameter of the calli was about 1.5-2 cm.

For regeneration, the calli were then cultured on PHI-E medium [MS salts 4.3 g/l; myo-inositol 0.1 g/l; nicotinic acid 0.5 mg/l, thiamine.HCl 0.1 mg/l, Pyridoxine.HCl-0.5 mg/l, Glycine 2.0 mg/l, Zeatin 0.5 mg/l, sucrose 60.0 g/l, Agar (Sigma, A-7049) 8.0 g/l, Indoleacetic acid (IAA, Sigma) 1.0 mg/l, Abscisic acid (ABA, Sigma) 0.1 mM, Bialaphos 3 mg/l, carbenicillin 100 mg/l adjusted to pH 5.6] in the dark at 28° C. for 1-3 weeks to allow somatic embryos to mature. The calli were then cultured on PHI-F medium (MS salts 4.3 g/l; myo-inositol 0.1 g/l; Thiamine.HCl 0.1 mg/l, Pyridoxine.HCl-0.5 mg/l, Glycine 2.0 mg/l, nicotinic acid 0.5 mg/l; sucrose 40.0 g/l; gelrite 1.5 g/l; pH 5.6] at 25.degree. C. under a daylight schedule of 16 hrs. light (270 uE $m^{-2}$ $sec^{-1}$) and 8 hrs. dark until shoots and roots developed. Each small plantlet was then transferred to a 25×150 mm tube containing PHI-F medium and grown under the same conditions for approximately another week. The plants were transplanted to pots with soil mixture in a greenhouse. GUS+ events are determined at the callus stage or regenerated plant stage.

For Hi-II, an optimized protocol was: 0.5×109 cfu/ml *Agrobacterium*, a 3-5 day resting step, and no AgNO3 in the infection medium (PHI-A medium).

Example 4

Confirmation of Expression by GUS Assay

Ability of the SB-LEG promoter and to drive expression in maize endosperm from 10-40 DAP were confirmed by histochemical localization of GUS activity in transgenic kernels using the method of Topping and Lindsey (Plant Molecular Biology—A Laboratory Manual, M. S. Clark (ed), Springer-Verlag, 1997, pp 436-438). No expression was detected in leaf tissue of the same plants.

Although the foregoing invention has been described in some detail by way of illustration and example for purposes of clarity of understanding, it will be obvious that certain changes and modifications may be practiced within the scope of the appended claims.

What is claimed is:

1. A plant stably transformed with an expression cassette comprising a regulatory element operably linked to a nucleotide sequence wherein the regulatory element comprises the nucleotide sequence of SEQ ID NO:4.

2. The plant of claim 1, wherein said plant is a monocot.

3. The plant of claim 2, wherein said monocot is maize, wheat, rice, barley, sorghum, or rye.

4. A seed of the plant of claim 1, wherein the seed comprises the expression cassette.

5. A method for expressing a nucleotide sequence in a plant, the method comprising:
   a) transforming a plant cell with an expression cassette, the expression cassette comprising an isolated regulatory element operably linked to a nucleotide sequence wherein the regulatory element comprises the nucleic acid sequence set forth in SEQ ID NO: 4;
   b) growing the plant cell to express the nucleotide sequence; and
   c) regenerating a stably transformed plant from the plant cell; wherein expression of the nucleotide sequence alters a phenotype of the plant.

6. A transformed plant obtained from the method of claim 5, wherein said plant is a monocot, and wherein said plant comprises the expression cassette.

7. The plant of claim 6, wherein said monocot is maize, wheat, rice, barley, sorghum, or rye.

8. A transformed seed obtained from the plant of claim 6, wherein said seed comprises the expression cassette.

* * * * *